United States Patent
Butcher et al.

(10) Patent No.: US 7,942,104 B2
(45) Date of Patent: May 17, 2011

(54) 3-DIMENSIONAL EMBROIDERY STRUCTURES VIA TENSION SHAPING

(75) Inventors: Peter Butcher, Nottingham (GB); Christopher Reah, Taunton (GB); Alan McLeod, Somerset (GB)

(73) Assignee: NuVasive, Inc., San Diego, CA (US)

( * ) Notice: Subject to any disclaimer, the term of this patent is extended or adjusted under 35 U.S.C. 154(b) by 469 days.

(21) Appl. No.: 11/968,155

(22) Filed: Dec. 31, 2007

(65) Prior Publication Data

US 2008/0173223 A1 Jul. 24, 2008

Related U.S. Application Data

(60) Provisional application No. 60/881,684, filed on Jan. 22, 2007.

(51) Int. Cl.
*D05B 93/00* (2006.01)
*B32B 7/08* (2006.01)

(52) U.S. Cl. ............................ 112/475.18; 112/403

(58) Field of Classification Search ............ 112/413, 112/416, 439, 102, 103, 117–119, 305, 475.18, 112/475.22, 403, 415; 606/246, 151, 152–157, 606/247–249
See application file for complete search history.

(56) References Cited

U.S. PATENT DOCUMENTS

| | | | | |
|---|---|---|---|---|
| 889,614 A | * | 6/1908 | Johnsen | 112/475.18 |
| 2,687,703 A | * | 8/1954 | Shotsky | 112/100 |
| 3,183,868 A | * | 5/1965 | Shotsky | 112/118 |
| 3,270,696 A | * | 9/1966 | Lowenstein | 112/475.22 |
| 3,859,941 A | | 1/1975 | Krieger | |
| 3,867,728 A | | 2/1975 | Stubstad et al. | |
| 3,875,595 A | | 4/1975 | Froning | |
| 4,280,954 A | | 7/1981 | Yannas et al. | |
| 4,309,777 A | | 1/1982 | Patil | |
| 4,349,921 A | | 9/1982 | Kuntz | |
| 4,415,617 A | | 11/1983 | D'Elia | |
| 4,458,678 A | | 7/1984 | Yannas et al. | |
| 4,512,038 A | | 4/1985 | Alexander et al. | |
| 4,714,469 A | | 12/1987 | Kenna | |
| 4,728,329 A | | 3/1988 | Mansat | |
| 4,759,766 A | | 7/1988 | Buettner-Janz | |
| 4,759,769 A | | 7/1988 | Hedman et al. | |
| 4,772,287 A | | 9/1988 | Ray et al. | |
| 4,776,851 A | | 10/1988 | Bruchman et al. | |
| 4,790,850 A | | 12/1988 | Dunn et al. | |
| 4,863,476 A | | 9/1989 | Shepperd | |
| 4,863,477 A | | 9/1989 | Monson | |
| 4,880,429 A | | 11/1989 | Stone | |

(Continued)

FOREIGN PATENT DOCUMENTS

DE 703123 C 1/1941

(Continued)

OTHER PUBLICATIONS

Notification of Transmittal of the International Search Report and the Written Opinion of the International Searching Authority in PCT/US2008/051828 mailed Jul. 18, 2008.

*Primary Examiner* — Ismael Izaguirre
(74) *Attorney, Agent, or Firm* — Jonathan Spangler; Marjorie Jarvis (57) ABSTRACT

An embroidery process allowing for a three-dimensional shape to be embroidered in two dimensions, allowing for the cost effective and repeatable manufacturing required for use in surgically implanted medical devices.

7 Claims, 4 Drawing Sheets

U.S. PATENT DOCUMENTS

| | | | |
|---|---|---|---|
| 4,904,260 | A | 2/1990 | Ray et al. |
| 4,905,692 | A | 3/1990 | More |
| 4,911,718 | A | 3/1990 | Lee et al. |
| 4,917,704 | A | 4/1990 | Frey et al. |
| 4,932,969 | A | 6/1990 | Frey et al. |
| 4,932,975 | A | 6/1990 | Main et al. |
| 4,946,377 | A | 8/1990 | Kovach |
| 4,946,378 | A | 8/1990 | Hirayama et al. |
| 4,955,908 | A | 9/1990 | Frey et al. |
| 5,002,576 | A | 3/1991 | Fuhrmann et al. |
| 5,004,474 | A | 4/1991 | Fronk et al. |
| 5,007,926 | A | 4/1991 | Derbyshire |
| 5,007,934 | A | 4/1991 | Stone |
| 5,047,055 | A | 9/1991 | Bao et al. |
| 5,108,438 | A | 4/1992 | Stone |
| 5,108,937 | A | 4/1992 | White |
| 5,123,926 | A | 6/1992 | Pisharodi |
| 5,171,280 | A | 12/1992 | Baumgartner |
| 5,171,281 | A | 12/1992 | Parsons et al. |
| 5,192,322 | A | 3/1993 | Koch et al. |
| 5,192,326 | A | 3/1993 | Bao et al. |
| 5,246,458 | A | 9/1993 | Graham |
| 5,258,043 | A | 11/1993 | Stone |
| 5,306,308 | A | 4/1994 | Gross et al. |
| 5,306,309 | A | 4/1994 | Wagner et al. |
| 5,383,884 | A | 1/1995 | Summers |
| 5,401,269 | A | 3/1995 | Buttner-Janz et al. |
| 5,443,499 | A | 8/1995 | Schmitt |
| 5,458,636 | A | 10/1995 | Brancato |
| 5,458,643 | A | 10/1995 | Oka et al. |
| 5,507,816 | A | 4/1996 | Bullivant |
| 5,522,898 | A | 6/1996 | Bao |
| 5,534,028 | A | 7/1996 | Bao et al. |
| 5,534,030 | A | 7/1996 | Navarro et al. |
| 5,540,688 | A | 7/1996 | Navas |
| 5,540,703 | A | 7/1996 | Barker, Jr. et al. |
| 5,545,229 | A | 8/1996 | Parsons et al. |
| 5,549,679 | A | 8/1996 | Kuslich |
| 5,562,736 | A | 10/1996 | Ray et al. |
| 5,562,738 | A | 10/1996 | Boyd et al. |
| 5,571,189 | A | 11/1996 | Kuslich |
| 5,609,119 | A * | 3/1997 | Yeh .................... 112/475.23 |
| 5,645,597 | A | 7/1997 | Krapiva |
| 5,674,296 | A | 10/1997 | Bryan et al. |
| 5,676,702 | A | 10/1997 | Ratron |
| 5,683,464 | A | 11/1997 | Wagner et al. |
| 5,683,465 | A | 11/1997 | Shinn et al. |
| 5,702,450 | A | 12/1997 | Bisserie |
| 5,702,454 | A | 12/1997 | Baumgartner |
| 5,705,780 | A | 1/1998 | Bao |
| 5,716,416 | A | 2/1998 | Lin |
| 5,755,796 | A | 5/1998 | Ibo et al. |
| 5,794,555 | A * | 8/1998 | Kwang .................... 112/475.22 |
| 5,800,543 | A | 9/1998 | McLeod et al. |
| 6,093,205 | A | 7/2000 | McLeod et al. |
| 6,110,210 | A | 8/2000 | Norton et al. |
| 6,174,330 | B1 | 1/2001 | Stinson |
| 6,248,106 | B1 | 6/2001 | Ferree |
| 6,283,998 | B1 | 9/2001 | Eaton |
| 6,368,326 | B1 | 4/2002 | Dakin et al. |
| 6,371,990 | B1 | 4/2002 | Ferree |
| 6,416,776 | B1 | 7/2002 | Shamie |
| 6,419,704 | B1 | 7/2002 | Ferree |
| 6,428,544 | B1 | 8/2002 | Ralph et al. |
| 6,447,548 | B1 | 9/2002 | Ralph et al. |
| 6,592,625 | B2 | 7/2003 | Cauthen |
| 6,620,196 | B1 | 9/2003 | Trieu |
| 6,712,853 | B2 | 3/2004 | Kuslich |
| 6,746,485 | B1 | 6/2004 | Zucherman et al. |
| 6,893,466 | B2 | 5/2005 | Trieu |
| 6,925,947 | B2 * | 8/2005 | Lin et al. .................... 112/475.22 |
| 6,955,689 | B2 | 10/2005 | Ryan et al. |
| 7,004,970 | B2 | 2/2006 | Cauthen II et al. |
| 7,214,225 | B2 * | 5/2007 | Ellis et al. .................... 606/60 |
| 7,338,531 | B2 * | 3/2008 | Ellis et al. .................... 623/23.74 |
| 7,341,601 | B2 | 3/2008 | Eisermann et al. |
| 7,445,634 | B2 | 11/2008 | Trieu |
| 7,588,574 | B2 | 9/2009 | Assell et al. |
| 7,713,463 | B1 * | 5/2010 | Reah et al. .................... 264/490 |
| 2001/0027319 | A1 | 10/2001 | Ferree |
| 2002/0077702 | A1 | 6/2002 | Castro |
| 2003/0074075 | A1 | 4/2003 | Thomas, Jr. et al. |
| 2003/0078579 | A1 | 4/2003 | Ferree |
| 2003/0129257 | A1 | 7/2003 | Nies et al. |
| 2003/0220691 | A1 | 11/2003 | Songer et al. |
| 2004/0039392 | A1 | 2/2004 | Trieu |
| 2004/0078089 | A1 | 4/2004 | Ellis et al. |
| 2004/0113801 | A1 | 6/2004 | Gustafson et al. |
| 2004/0243237 | A1 | 12/2004 | Unwin et al. |
| 2005/0027364 | A1 | 2/2005 | Kim et al. |
| 2005/0119725 | A1 | 6/2005 | Wang et al. |
| 2005/0177240 | A1 | 8/2005 | Blain |
| 2005/0192669 | A1 | 9/2005 | Zdeblick et al. |
| 2005/0228500 | A1 | 10/2005 | Kim et al. |
| 2006/0085080 | A1 | 4/2006 | Bechgaard et al. |
| 2006/0116774 | A1 | 6/2006 | Jones et al. |
| 2006/0179652 | A1 | 8/2006 | Petersen et al. |
| 2006/0200137 | A1 | 9/2006 | Soboleski et al. |
| 2006/0293662 | A1 | 12/2006 | Boyer, II et al. |
| 2007/0055373 | A1 | 3/2007 | Hudgins et al. |
| 2007/0100453 | A1 | 5/2007 | Parsons et al. |
| 2007/0112428 | A1 | 5/2007 | Lancial |
| 2007/0204783 | A1 * | 9/2007 | Chong .................... 112/475.22 |

FOREIGN PATENT DOCUMENTS

| | | |
|---|---|---|
| DE | 383005 C1 | 11/1989 |
| DE | 4315757 C1 | 11/1994 |
| EP | 0117072 A1 | 1/1984 |
| EP | 0192949 A1 | 9/1986 |
| EP | 0260970 A2 | 3/1988 |
| EP | 0179695 B1 | 3/1989 |
| EP | 0314412 A1 | 5/1989 |
| EP | 0328401 A1 | 8/1989 |
| EP | 0334045 A1 | 9/1989 |
| EP | 0346129 A1 | 12/1989 |
| EP | 0346269 A2 | 12/1989 |
| EP | 0453393 A1 | 10/1991 |
| EP | 0298235 B1 | 12/1991 |
| EP | 0459914 A1 | 12/1991 |
| EP | 0621017 A1 | 4/1994 |
| EP | 0599419 A2 | 6/1994 |
| EP | 0621010 A1 | 10/1994 |
| EP | 0662309 A1 | 7/1995 |
| EP | 0563332 B1 | 8/1995 |
| EP | 0820740 A1 | 1/1996 |
| EP | 0744162 A2 | 11/1996 |
| EP | 0747025 A1 | 12/1996 |
| EP | 1318167 A2 | 6/2003 |
| FR | 2638349 A1 | 5/1988 |
| FR | 2688691 A1 | 9/1993 |
| FR | 2690073 A1 | 10/1993 |
| FR | 2696338 A1 | 4/1994 |
| FR | 2700810 A3 | 7/1994 |
| FR | 2710520 A1 | 4/1995 |
| FR | 2710829 A1 | 4/1995 |
| GB | 2270264 A | 3/1994 |
| GB | 2276823 A | 10/1994 |
| WO | WO 90/11735 A1 | 10/1990 |
| WO | WO 90/12551 A1 | 11/1990 |
| WO | WO 91/00713 A1 | 1/1991 |
| WO | WO 91/03993 A1 | 4/1991 |
| WO | WO 92/03988 A1 | 3/1992 |
| WO | WO 92/10218 A1 | 6/1992 |
| WO | WO 92/10982 A1 | 7/1992 |
| WO | WO 93/16664 A1 | 9/1993 |
| WO | WO 93/17635 A1 | 9/1993 |
| WO | WO 95/19153 A1 | 7/1995 |
| WO | WO 95/25487 A1 | 9/1995 |
| WO | WO 95/31946 A1 | 11/1995 |
| WO | WO 96/11639 A1 | 4/1996 |
| WO | WO 96/11642 A1 | 4/1996 |
| WO | WO 96/40014 A1 | 12/1996 |
| WO | WO 97/20526 A1 | 6/1997 |
| WO | WO 99/37242 A1 | 7/1999 |
| WO | WO 01/21246 A1 | 3/2001 |
| WO | WO 01/30269 A1 | 5/2001 |
| WO | WO 02/11650 A1 | 2/2002 |

| WO | WO 02/30306 A1 | 4/2002 |
| WO | WO 02/30324 A1 | 4/2002 |
| WO | WO 03/06811 A1 | 8/2003 |
| WO | WO 2004/002374 A1 | 1/2004 |
| WO | WO 2005/004941 A1 | 1/2005 |
| WO | WO 2005/092211 A1 | 10/2005 |
| WO | WO 2005/092247 A1 | 10/2005 |
| WO | WO 2005/092248 A1 | 10/2005 |
| WO | WO 2005/133130 A2 | 12/2006 |
| WO | WO 2007/012070 A2 | 1/2007 |
| WO | WO 2007/020449 A2 | 2/2007 |
| WO | WO 2007/067547 A2 | 6/2007 |

* cited by examiner

3-DIMENSIONAL EMBROIDERY STRUCTURES VIA TENSION SHAPING

CROSS REFERENCES TO RELATED APPLICATIONS

The present application is a nonprovisional patent application claiming benefit under 35 U.S.C. §119(e) from U.S. Provisional Application Ser. No. 60/881,684, filed on Jan. 22, 2007, the entire contents of which are hereby expressly incorporated by reference into this disclosure as if set forth fully herein.

BACKGROUND OF THE INVENTION

I. Field of the Invention

The present invention relates to medical devices and methods generally aimed at surgical implants. In particular, the disclosed system and associated methods are related to a manner of creating surgical implants via embroidery.

II. Discussion of the Prior Art

Embroidered structures are created on substrates. Some substrates are designed to stay in place with the embroidered structure while other substrates are removed at the end of the embroidery process. All of the embroidered structures discussed below are created on removable substrates, specifically ones removed through processes of dissolution.

On a dissolvable substrate, a plurality of parallel, stationary backing threads are placed and secured on one surface of a dissolvable substrate, called the backing surface. On the opposing surface of the substrate, called the stitching surface, is a plurality of stitching threads with one-to-one correspondence to the backing threads. Stitching may be done between one pair of threads at a time or in simultaneous multiplicity, as is described below.

The plurality of stitching threads from the stitching surface are passed through openings created in the dissolvable substrate by the passing of each individual thread to the backing surface. Each stitching thread is then looped over its corresponding backing thread, in essence picking up the backing thread, forming a lock stitch. Once each stitching thread has picked up its corresponding backing thread, the plurality of stitching threads are passed from the backing surface to the stitching surface through the openings in the dissolvable substrate created during the passage to the backing surface. The lock stitches prevent the stitching threads from completely pulling back out of the openings created in the dissolvable substrate. The plurality of stitching threads is then moved to a new stitching site and the process repeats until all the backing threads are joined by lock stitches to the corresponding stitching threads, creating a plurality of thread pairs.

A plurality of thread pairs may be enclosed by one or more pluralities of enclosing thread pairs. To enclose a plurality of thread pairs, a plurality of enclosing backing threads are placed and secured on the backing surface of a dissolvable substrate already holding at least one plurality of thread pairs, such that the plurality of enclosing backing threads covers the previously stitched plurality of backing threads. A plurality of enclosing backing threads is usually not parallel with the previous plurality of backing and stitching threads. A plurality of enclosing stitching threads, with one-to-one correspondence to the plurality of enclosing backing threads, are then stitched to the plurality of enclosing backing threads by the stitching process described above.

When the enclosing backing threads are all joined to the enclosing stitching threads by lock stitches, a plurality of enclosing thread pairs has been formed. This process may be repeated by stitching even more pluralities of enclosing thread pairs over all the previously stitched thread pairs, such that the first plurality is enclosed by the second plurality, which is enclosed by a third plurality, which is enclosed by a fourth plurality, etc. This process produces stable embroidered structures which do not unstitch into a pile of threads when the dissolvable substrate is removed.

The process of dissolvable substrate removal is dependent upon the composition of the dissolvable substrate material. Substrate materials are chosen such that the dissolution process which removes the dissolvable substrate will minimally, if at all, affect the physical properties of the remaining embroidered structure. The embroidered structure remains intact despite the removal of the dissolvable substrate because each stitching thread is stitched to its corresponding backing thread and vice versa. The backing thread is enclosed in one or more pluralities of enclosing thread pairs, which provides structural support. The result of the stitching is the creation of a generally two dimensional embroidered structure. There are, however, applications where it would be advantageous to have a generally three-dimensional embroidered structure rather than a generally two-dimensional embroidered structure, but the processes by which three-dimensional embroidered structures may be formed have been complicated and not conducive to cost effective and repeatable mass production.

The first type of process for creating three-dimensional embroidered structures has been to build up the structural shape of the embroidered structure with layer upon layer of embroidered thread. The drawbacks to this technique are that it makes the embroidered structure thicker where the building up had been done. The building up only yields block-type structures and does not allow for the embroidering of curvatures.

A second process of manufacturing three-dimensional embroidered structures takes two or more generally flat embroidered structures and stitches them together such that they form a three-dimensional structure. While preserving the uniform thickness of the embroidered structures lost by the layering technique above and allowing for the simplicity of embroidering each flat section in two-dimensions, this process requires several stitching steps, that would typically be performed manually, which must be done three-dimensionally after the embroidering of the sections is completed. This process is costly, with repeatability concerns where the final results and dimensions will be subject to the skill and dexterity of the individual who performs the stitching.

A third known process creates a single, generally two-dimensional embroidered structure which may be folded such that the edge or edges of the structure meet and may be stitched together, again typically by a manual process, to form a three-dimensional structure. However, this process suffers from the same post-embroidering stitching steps in three-dimensions as the second process, and thus suffers from the same drawbacks.

The present invention is intended to deal with these and other limitations of creating three-dimensional embroidered structures cost effectively and repeatably.

SUMMARY OF THE INVENTION

According to the present invention, there is provided a manufacturing process performed on a two-dimensional substrate which produces three-dimensional embroidered structures which may be produced in a cost effective, repeatable manner.

The two-dimensional substrate upon which the embroidery is to be manufactured is tensioned throughout the manufacturing process. Load bearing threads are laid down under tension on the substrate, further tensioning the substrate such that tension gradients are present and different positions on the substrate will be under different amounts of tension. A backing mesh in the general shape of a hexagon or other generally polygonal or non-polygonal shape is then manufactured over the load bearing threads on the substrate. The backing mesh may be manufactured using customary techniques of embroidery, or any other process which results in the backing mesh having qualities similar to those of normally embroidered structures. The effect of the load bearing threads and backing mesh being embroidered on the substrate, and the different tensions at different points on the substrate, cause the load bearing threads to be relationally shorter than the threads forming the backing mesh. When the substrate upon which the embroidered structure was manufactured is removed from the embroidered structure, the load bearing threads and backing mesh are no longer being externally tensioned, allowing the load bearing threads and backing mesh to relax. The relationally shorter load bearing threads relax more than the relationally longer backing mesh, and this difference in magnitude of relaxation results in the load bearing threads drawing the backing mesh inward, forcing the backing mesh into a three-dimensional shape having varying three-dimensional properties.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF PREFERRED EMBODIMENT

An illustrative embodiment of the invention is described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The process of creating three-dimensional embroidered structures through differential tensioning of a two-dimensional substrate upon which the embroidered structure is manufactured disclosed herein boasts a variety of inventive features and components that warrant patent protection, both individually and in combination.

Figure 1:
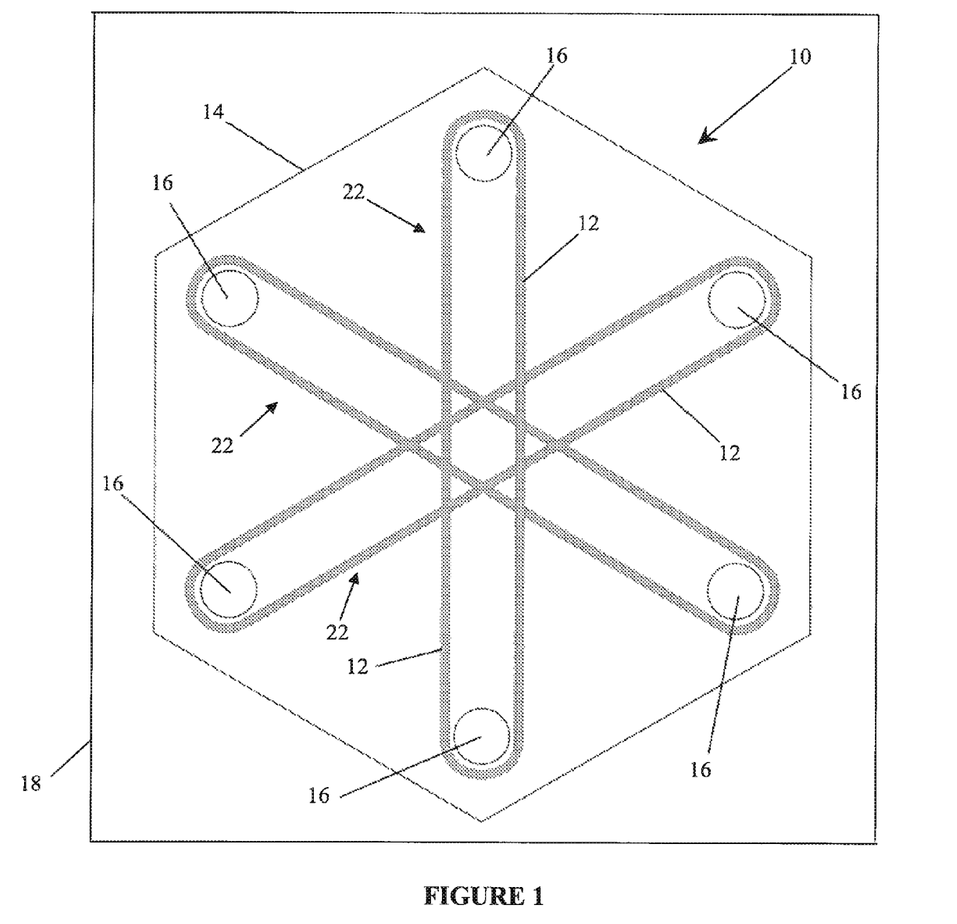
FIG. 1 is a plan view of the load bearing threads and backing mesh of the embroidered structure on the tensioned substrate.

FIG. 1 shows an embroidered structure 10 manufactured according to the present invention. A substrate 18 formed from acetate or any other material suitable for use as a dissolvable substrate for embroidery is prepared by being placed under tension from its edges. Load bearing threads 12 are then laid down under tension on the tensioned substrate 18, further tensioning the substrate 18 such that tension gradients are present and different positions on the substrate will be under different amounts of tension. The load bearing threads 12 may be formed from any suitable material for creating an embroidered structure, including but not limited to polyester, polypropylene, polyethylene, carbon fiber, glass, glass fiber, polyaramide, metal, copolymers, polylactic acid, polyglycolic acid, biodegradable fibers, silk, cellulosic and polycaprolactone, including mixtures of one or more of these materials including fibers made therefrom. Once the load bearing threads 12 are in place, a backing mesh 14 may be embroidered, woven or manufactured by any other customary process which results in the backing mesh having qualities similar to those of normally embroidered structures, around the load bearing threads 12. The backing mesh 14 maybe be any suitable shape, including by not limited to generally hexagonal, polygonal or non-polygonal. The backing mesh 14 may be formed from the same or different materials as the load bearing threads 12. The embroidering of load bearing threads 12 and backing mesh 14 on a substrate which is subject to tension in a gradient of positional dependence causes the load bearing threads 12 to be relationally shorter than the threads forming the backing mesh 14. Surrounding structures may be engineered to form eyelets 16 or other formations to which the load bearing threads 12 may attach.

One exemplary embodiment of the present invention as shown in FIG. 1 includes a backing mesh 14 that is generally hexagonal in shape. According to this embodiment, the backing mesh 14 includes at least one eyelet 16 in each of the six vertices. The load bearing threads 12 are positioned on the backing mesh 14 such that the load bearing threads 12 form at least three thread paths 22, with each thread path 22 encircling at least two eyelets 16 that are located directly opposite of each other on the backing mesh 14. Each thread path 22 bisects the hexagonal backing mesh 14 between two vertices. Further, each thread path 22 bisects each of the other two thread paths 22. The load bearing threads 12 may be positioned along these thread paths 22 at least once and possibly multiple times. Lock stitching and layering will prevent the device from loosening or unraveling.

Figure 2:
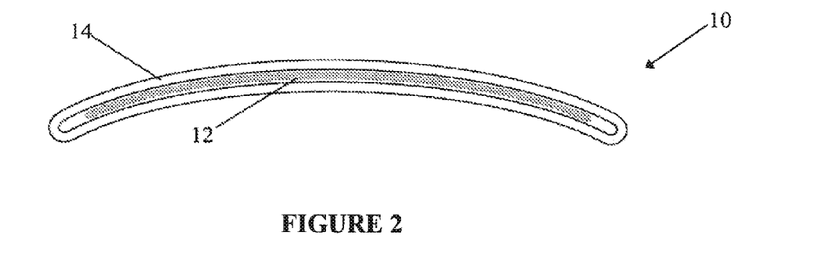
FIG. 2 is a cross-sectional view of the load bearing threads and backing mesh of the embroidered structure of FIG. 1 after removal of the tensioned substrate.

FIG. 2 shows a cross-section of the embroidered structure 10 after removal of the tensioned substrate 18. When the substrate 18 is dissolved or otherwise removed from the embroidered structure 10, the substrate tension dissipates. In the absence of the tension provided by the substrate 18, both the load bearing threads 12 and backing mesh 14 relax. The relationally shorter load bearing threads 12 relax more than the relationally longer backing mesh 14, and this difference in magnitude of relaxation results in the load bearing threads 12 drawing the backing mesh 14 inward, forcing the backing mesh 14 into a three-dimensional shape.

Figure 3A:
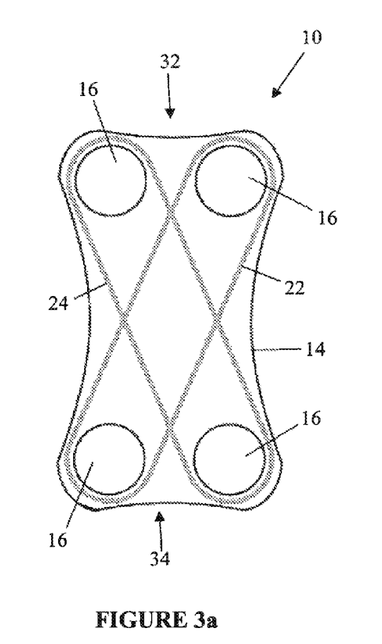
FIG. 3a is a plan view of the load bearing threads and backing mesh of the embroidered structure according to an alternative embodiment of the present invention for single level application.
Figure 3B:
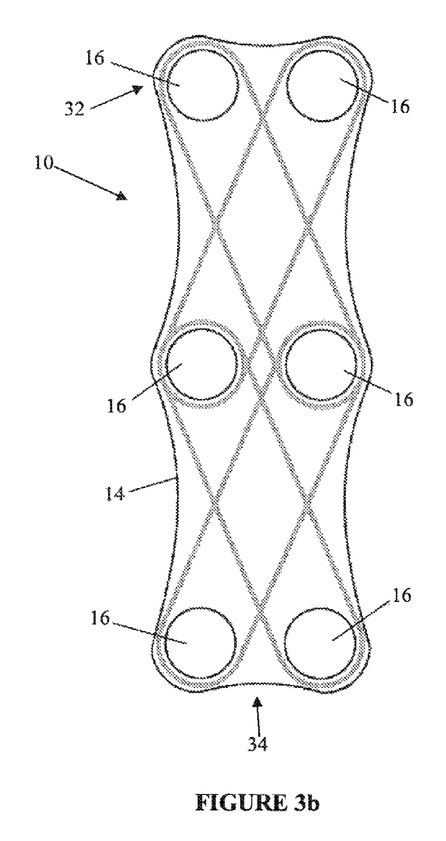
FIG. 3b is a plan view of the load bearing threads and backing mesh of the embroidered structure according to an alternative embodiment of the present invention for a multi-level application.

FIGS. 3a-b illustrate an alternative embodiment of the present invention which may, by way of example only, be used as an anterior cervical plate to prevent egress of a cervical implant post-implantation. The embroidered structure 10 of the present invention serves as a buttress to keep the cervical implant inside the disc space after the cervical implant has been placed. The embodiment of FIG. 3a includes a backing mesh 14 that is generally rectangular in shape with mild concave curvatures expending along each side between successive eyelets 16. According to this embodiment, the backing mesh 14 includes a pair of eyelets 16 on each of the upper portion 32 and lower portion 34 of the backing mesh 14. The load bearing threads 12 are positioned on the backing mesh 14 such that the load bearing threads 12 form at least two thread paths 22, 24, with each path encircling at least two eyelets 16 that are located directly opposite of each other on the backing mesh 14. Each individual thread path 22, 24 bisects the rectangular backing mesh 14 between two vertices. Further, each thread path 22, 24 bisects the other thread path 22.

Figure 4:
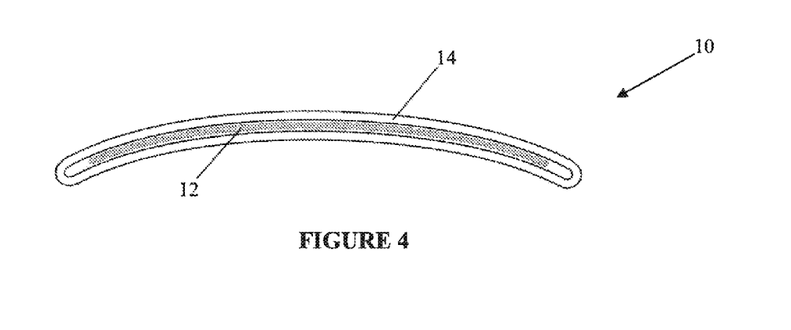
FIG. 4 is a cross-sectional view of the load bearing threads and backing mesh of the embroidered structure of FIGS. 3a-b.

FIG. 3b illustrates the embodiment of the present invention as shown in FIG. 3a adapted, by way of example only, for use as a multi-level anterior cervical plate. According to this embodiment, the backing mesh 14 includes a pair of eyelets 16 in each of the upper and lower portions 32, 34 and at least one pair of eyelets 16 positioned between the upper and lower portions of the backing mesh 14 with mild concave curvatures expending along each side between successive eyelets 16. The load bearing threads 12 are positioned on the backing mesh 14 in the same pattern as drawn in FIG. 3a, encircling diagonal pairs of eyelets 16 located on the lower portion of the backing mesh 14 and the pair of eyelets 16 located in the middle of the backing mesh 16. The same pattern is repeated around the middle pair of eyelets 16 and the pair of eyelets 16 located on the upper portion of the backing mesh 14. FIG. 4 shows a cross-section of the embroidered structure 10 according to the embodiments drawn in FIGS. 3a-b after removal of the tensioned substrate 18 resulting in a three-dimensional shape.

Figures 5A, 5B, 6:
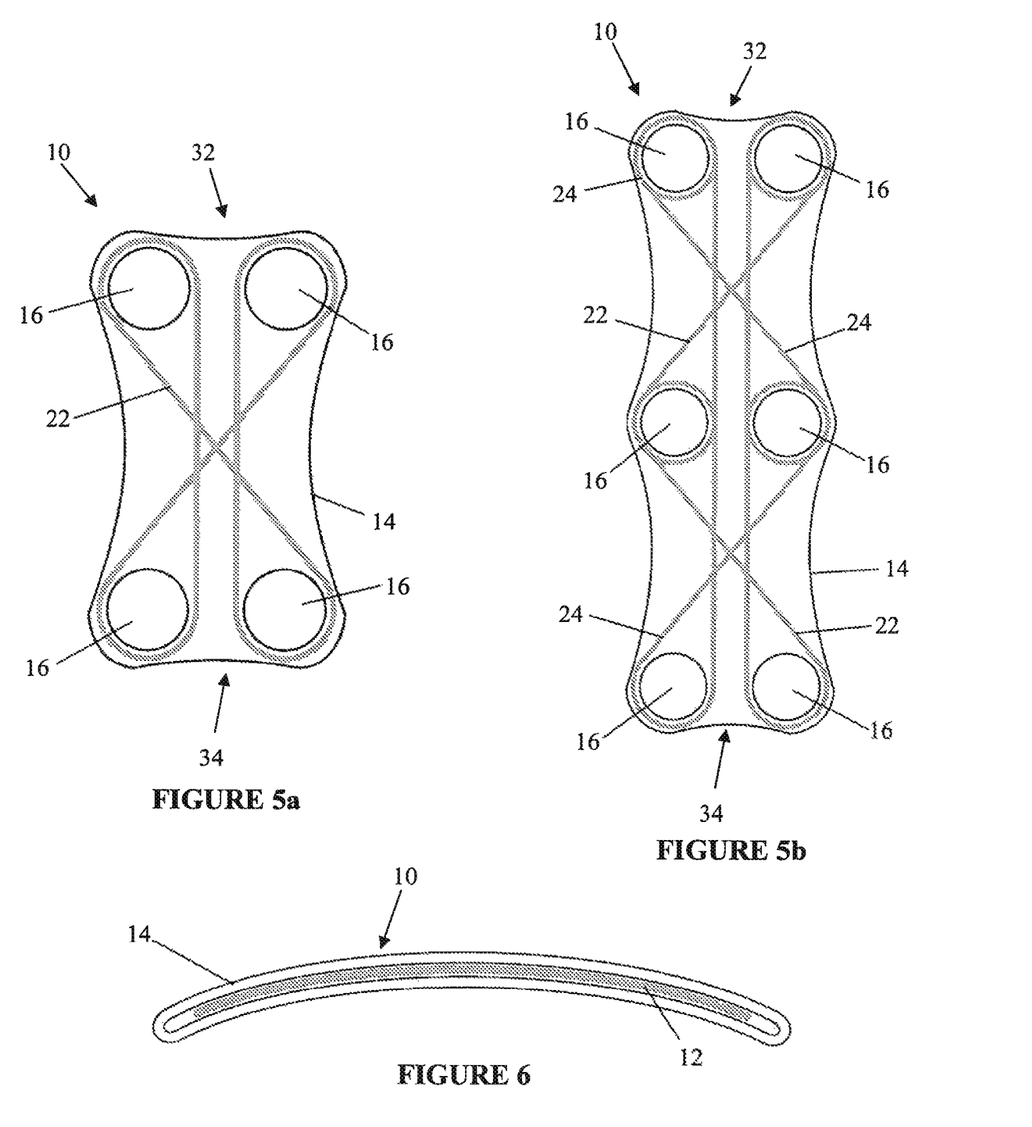
FIG. 5a is a plan view of the load bearing threads and backing mesh of the embroidered structure according to an alternative embodiment of the present invention for a single level application.
FIG. 5b is a plan view of the load bearing threads and backing mesh of the embroidered structure according to an alternative embodiment of the present invention for a multi-level application.
FIG. 6 is a cross-sectional view of the load bearing threads and backing mesh of the embroidered structure of FIGS. 5a-b.

FIGS. 5a-b illustrate another alternative embodiment of the present invention which, by way of example only, may be used as an anterior cervical plate to prevent egress of a cervical implant post-implantation. The embodiment drawn in FIG. 5a includes a backing mesh 14 that is generally rectangular in shape with mild concave curvatures expending along each side between successive eyelets 16. According to this embodiment, the backing mesh 14 includes a pair of eyelets 16 in each of the upper portion 32 and lower portion 34 of the backing mesh 14. The load bearing threads 12 are positioned on the backing mesh 14 such that the load bearing threads 12 form a thread path 22. The thread path 22 loops around the medial sides of the upper left eyelet 16 and the lower left eyelet 16. The thread path 22 then loops around the lateral side of the lower left eyelet 16, and then extends to and around the lateral side of the upper right eyelet 16. The thread path 22 then loops around the medial sides of the upper right eyelet 16 and the lower right eyelet 16. The thread path 22 continues around the lateral side of the lower right eyelet 16 and then extends to and around the lateral side of the upper left eyelet 16.

FIG. 5b illustrates the embodiment of the present invention as drawn in FIG. 5a adapted, by way of example only, for use as a multi-level anterior cervical plate. According to this embodiment, the backing mesh 14 includes a pair of eyelets 16 in each of the upper portion 32, middle portion 36 and lower portion 34 of the backing mesh 14 with mild concave curvatures expending along each side between successive eyelets 16. The load bearing threads 12 are positioned on the backing mesh 14 such that the load bearing threads 12 form at least two thread paths 22, 24. The first thread path 22 extends around the medial sides of the upper left eyelet 16, middle left eyelet 16 and the lower left eyelet 16, and then loops around the lateral side of the lower left eyelet 16. The thread path 24 then continues to loop around the lateral side of the middle right eyelet 16, and then extends to and around the lateral side of the upper left eyelet 16. The second thread path 24 extends along the medial sides of the upper right eyelet 16, middle right eyelet 16 and lower right eyelet 16, and loops around the lateral side of the lower right eyelet 16. The thread path 24 then loops around the lateral side of the middle left eyelet 16 and then extends to and loops around the lateral side of the upper right eyelet 16. FIG. 6 shows a cross-section of the embroidered structure 10 according to the embodiments drawn in FIGS. 5a-b after removal of the tensioned substrate 18.

Figure 7A:
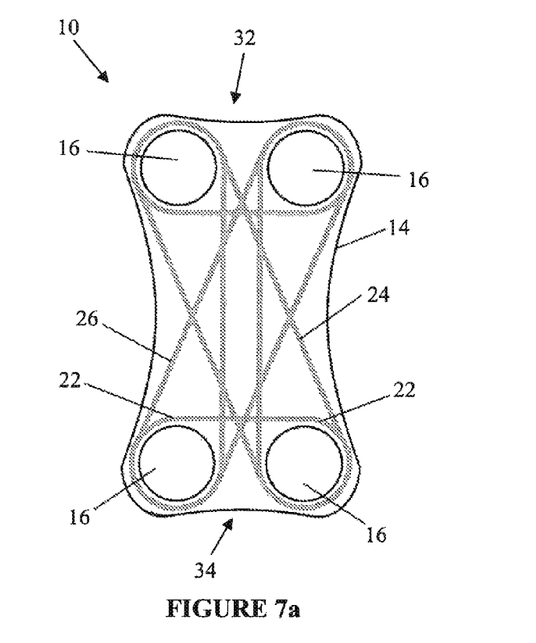
FIG. 7a is a plan view of the load bearing threads and backing mesh of the embroidered structure according to an alternative embodiment of the present invention for a single level application.
Figure 7B:
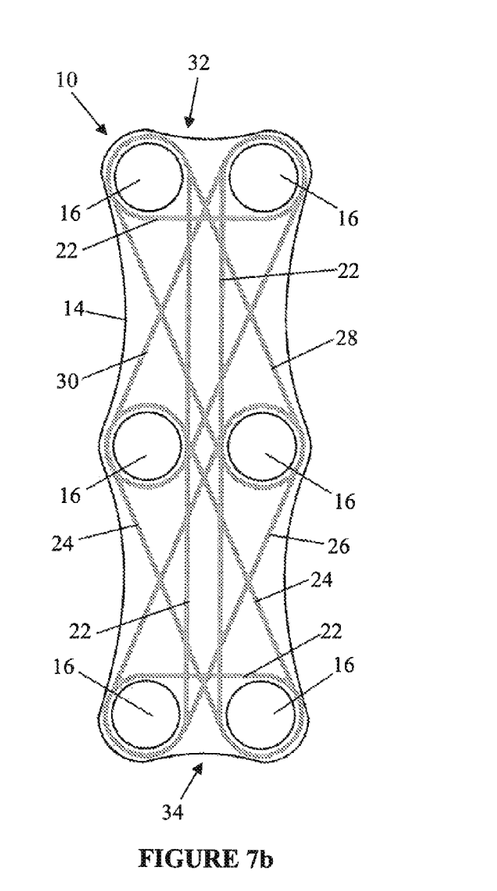
FIG. 7b is a plan view of the load bearing threads and backing mesh of the embroidered structure according to an alternative embodiment of the present invention for a multi-level application.

FIGS. 7a-b illustrate yet another alternative embodiment of the present invention which, by way of example only, may be used as an anterior cervical plate to prevent egress of a cervical implant post-implantation. The embodiment drawn in FIG. 7a includes a backing mesh 14 that is generally rectangular in shape with mild concave curvatures expending along each side between successive eyelets 16. According to this embodiment, the backing mesh 14 includes a pair of eyelets 16 in each of the upper portion 32 and lower portion 34 of the backing mesh 14. The load bearing threads 12 are positioned on the backing mesh 14 such that the load bearing threads 12 form at least three thread paths 22, 24, 26. The first thread path 22 extends along the medial sides of the upper left eyelet 16 and the lower left eyelet 16. The thread 22 then loops around the lateral side of the lower left eyelet 16, and then extends to and around the lateral side of the lower right eyelet 16. The thread 22 then loops around the medial sides of the lower right eyelet 16 and the upper right eyelet 16. The thread path 22 continues around the lateral side of the upper right eyelet 16 and then extends to and around the lateral side of the upper left eyelet 16.

The second and third thread paths 24, 26 encircle at least two eyelets 16 that are located diagonally opposite of each other on the backing mesh 14. Each of the second and third thread paths 24, 26 bisects the rectangular backing mesh 14 between two vertices. Further, each of the second and third thread paths 24, 26 bisects the other individual thread path 24, 26.

FIG. 7b illustrates the embodiment of the present invention as drawn in FIG. 7a adapted, by way of example only, for use as a multi-level anterior cervical plate. According to this embodiment, the backing mesh 14 includes a pair of eyelets 16 in each of the upper portion 32, middle portion 36 and lower portion 34 of the backing mesh 14 with mild concave curvatures expending along each side between successive eyelets 16. The load bearing threads 12 are positioned on the backing mesh 14 such that the load bearing threads 12 form at least five individual thread paths 22, 24, 26, 28, 30. The first thread path 22 extends around the medial sides of the upper left eyelet 16, middle left eyelet 16 and the lower left eyelet 16, and then loops around the lateral side of the lower left eyelet 16. The thread 22 then extends to and loops around the lateral side of the lower right eyelet 16, and then extends along the medial sides of the lower right, middle right and upper right eyelets 16. The thread 22 then loops around the upper right eyelet 16, and then extends to and loops around the upper left eyelet 16.

Figure 8:
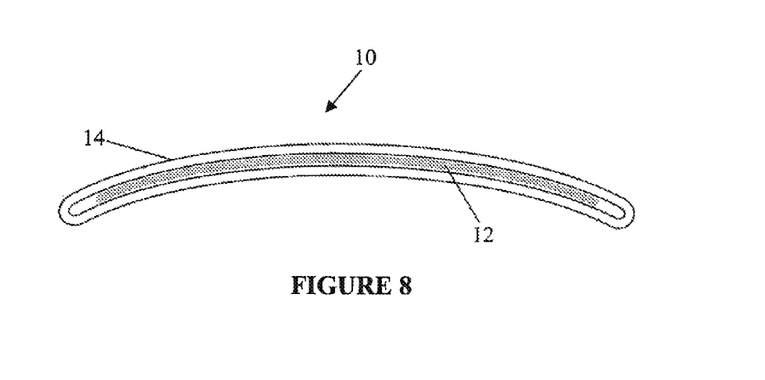
FIG. 8 is a cross-sectional view of the load bearing threads and backing mesh of the embroidered structure of FIGS. 7a-b.

The second thread path 24 encircles the lower right and the middle left eyelets 16. The third thread path 26 encircles the lower left and middle right eyelets 16. The second and third thread paths 24, 26 bisect each other. The fourth thread path 28 encircles the middle right and the upper left eyelets 16. The fifth thread path 30 encircles the middle left and upper right eyelets 16. The fourth and fifth thread paths 28, 30 bisect each other. FIG. 8 shows a cross-section of the embroidered structure 10 according to the embodiments drawn in FIGS. 7a-b after removal of the tensioned substrate 18.

The tension shaping of a generally two-dimensional embroidered structure into a three-dimensional structure allows for embroidered structures to be manufactured using automated devices such as commercially available embroidery machines, making the production of such embroidered structures cost effective and repeatable, as the production does not require hand stitching. The tension shaped embroidered structures are pulled into three-dimensional shapes and not built up out of extra material. This allows for the tension shaped embroidered structures to be produced in various three-dimensional shapes instead of only generally block shapes. The tension shaped embroidered structures are comparatively thin, retaining their flexibility compared to embroidered structures produced by the building up of additional material.

While the invention is susceptible to various modifications and alternative forms, a specific embodiment thereof has been shown by way of example in the drawings and is herein described in detail. It should be understood, however, that the description herein of a specific embodiment is not intended to limit the invention to the particular form disclosed, but on the contrary, the invention is to cover all modifications, equivalents, and alternatives falling within the spirit and scope of the invention as defined herein.

What is claimed is:

1. A method of manufacturing a three-dimensional textile structure, comprising:
   (a) providing a substrate having a stitching surface, a backing surface, and a plurality of edges, said substrate provided under tension from at least one of said edges;
   (b) introducing a plurality of load-bearing threads onto said stitching surface, said load-bearing threads introduced under tension;
   (c) introducing a plurality of backing threads forming a backing mesh onto said backing surface, said backing mesh introduced under tension; and
   (d) removing said substrate such that said load-bearing threads and said backing mesh relax to from a three-dimensional structure.

2. The method of claim 1, wherein step (b) further tensions the substrate forming tension gradients on the substrate such that different portions of the substrate will be under different amounts of tension.

3. The method of claim 2, wherein said load-bearing threads are relationally shorter than said backing threads.

4. The method of claim 3, wherein said relationally shorter load-bearing threads relax at a greater magnitude than said backing threads such that said backing mesh is forced into a three-dimensional shape.

5. The method of claim 1, wherein said load-bearing threads are formed of at least one of polyester, polypropylene, polyethylene, carbon fiber, glass, glass fiber, polyaramide, metal, copolymers, polylactic acid, polyglycolic acid, biodegradable fibers, silk, cellulosic, and polycaprolacotone.

6. The method of claim 1, wherein step (c) further comprises engaging said backing mesh said load-bearing threads by at least one of embroidery and weaving.

7. The method of claim 1, wherein the three-dimensional textile structure comprises at least one eyelet suitable for attachment to at least one vertebra of the spine.

* * * * *